United States Patent
Kurotani

(10) Patent No.: US 10,105,309 B2
(45) Date of Patent: Oct. 23, 2018

(54) SOLID POWDER COSMETIC

(71) Applicant: KOSE Corporation, Tokyo (JP)

(72) Inventor: Satoru Kurotani, Tokyo (JP)

(73) Assignee: KOSE Corporation, Tokyo (JP)

(*) Notice: Subject to any disclaimer, the term of this patent is extended or adjusted under 35 U.S.C. 154(b) by 0 days.

(21) Appl. No.: 15/561,215

(22) PCT Filed: Mar. 25, 2016

(86) PCT No.: PCT/JP2016/001759
§ 371 (c)(1),
(2) Date: Sep. 25, 2017

(87) PCT Pub. No.: WO2016/157869
PCT Pub. Date: Oct. 6, 2016

(65) Prior Publication Data
US 2018/0064631 A1    Mar. 8, 2018

(30) Foreign Application Priority Data

Mar. 30, 2015 (JP) ................. 2015-070229

(51) Int. Cl.
*A61K 8/898* (2006.01)
*A61K 8/29* (2006.01)
*A61K 8/81* (2006.01)
*A61K 8/02* (2006.01)
*A61K 8/25* (2006.01)
*A61K 8/26* (2006.01)
*A61Q 1/12* (2006.01)
*A61Q 1/10* (2006.01)
*A61Q 1/08* (2006.01)

(52) U.S. Cl.
CPC ............. *A61K 8/898* (2013.01); *A61K 8/022* (2013.01); *A61K 8/25* (2013.01); *A61K 8/26* (2013.01); *A61K 8/29* (2013.01); *A61K 8/8158* (2013.01); *A61Q 1/08* (2013.01); *A61Q 1/10* (2013.01); *A61Q 1/12* (2013.01); *A61K 2800/624* (2013.01)

(58) Field of Classification Search
None
See application file for complete search history.

(56) References Cited

U.S. PATENT DOCUMENTS

2012/0308499 A1* 12/2012 Vic .................. A61K 8/25
424/63

FOREIGN PATENT DOCUMENTS

| JP | 60192037 | | 7/1994 |
|---|---|---|---|
| JP | 09227338 A | * | 9/1997 |
| JP | 2000-344616 | | 12/2000 |
| JP | 3522297 | | 2/2004 |
| JP | 2004-182729 | | 7/2004 |
| JP | 2006282583 A | * | 10/2006 |
| JP | 2010-163368 | | 7/2010 |
| JP | 2013-35783 | | 2/2013 |
| JP | 2014-91735 | | 5/2014 |

OTHER PUBLICATIONS

Notification of Transmittal of Translation of the International Preliminary Report on Patentability and the International Preliminary Report on Patentability issued by The International Bureau of WIPO dated Oct. 12, 2017, 8 pages.

* cited by examiner

*Primary Examiner* — Robert A Wax
*Assistant Examiner* — Caralynne E Helm
(74) *Attorney, Agent, or Firm* — Occhiuti & Rohlicek LLP

(57) ABSTRACT

The present invention provides a solid powder cosmetic exhibiting excellent ease of loosening of the cosmetic, smooth feeling in use, and adhesiveness to the skin and also exhibiting no change in usability in continuous use and having excellent filling and molding properties and drop strength. The invention relates to a solid powder cosmetic containing following components (A), components (B), and components (C); (A) a powder, (B) a (sodium acrylate/sodium acryloyldimethyl taurate) copolymer, and (C) a water-swelling clay mineral.

19 Claims, No Drawings

SOLID POWDER COSMETIC

CROSS REFERENCE TO RELATED APPLICATIONS

This application is a National Phase under 35 USC 371 of International Application No. PCT/JP2016/001759 filed on Mar. 25, 2016, which claims priority to Japanese Application No. 2015-070229 filed Mar. 30, 2015, the contents of which are hereby incorporated by reference in their entirety.

TECHNICAL FIELD

The present invention relates to a solid powder cosmetic.

BACKGROUND ART

Solid powder cosmetics produce various senses, textures, and color tones by changing the compositions and contents of oils, color pigments, glitter powders, extender powders, and excipients. However, in recent solid powder cosmetics, not only esthetics by color tones and pearl feeling but also trials, such as filling of containers having complicated shapes and three-dimensional molding, have been performed for further enhancing the designs of cosmetics.

However, an improvement in the filling and molding properties of a cosmetic for filling of a container having a complicated shape or for three-dimensional molding decreases the ease of loosening of the cosmetic and the smooth feeling in use, whereas an improvement in the ease of loosening of a cosmetic or the smooth feeling in use decreases the drop strength of the molded product.

For this problem, for example, a technique of increasing the strength of a cosmetic by molding an aqueous solvent containing a powder and a water-swelling clay mineral into a spherical shape (Patent Document 1) or a technique of improving the drop strength and the soft feeling in use by using a fatty acid aluminum salt (Patent Document 2) has been investigated.

PRIOR ART DOCUMENTS

Patent Documents

Patent Document 1: Japanese Patent No. 3522297
Patent Document 2: Japanese unexamined Patent Application Publication No. 2010-163368

SUMMARY OF THE INVENTION

Object to be Solved by the Invention

However, although these techniques can increase the drop strength, the ease of loosening of the cosmetic and the smooth feeling in use are insufficient.

Accordingly, it is an object of the present invention to provide a solid powder cosmetic exhibiting excellent ease of loosening of the cosmetic, smooth feeling in use, and adhesiveness to the skin and exhibiting no change in usability in continuous use and having excellent filling and molding properties and drop strength.

Means to Solve the Object

In the light of such circumstances, the present inventor intensively studied and, as a result, found that a solid powder cosmetic exhibiting excellent ease of loosening of the cosmetic, smooth feeling in use, and adhesiveness to the skin and exhibiting no change in usability in continuous use and having excellent filling and molding properties and drop strength can be given by mixing a powder, a (sodium acrylate/sodium acryloyldimethyl taurate) copolymer, and a water-swelling clay mineral and accomplished the present invention.

That is, the present invention relates to:
(1) A solid powder cosmetic comprising components (A) to (C):
(A) a powder,
(B) a (sodium acrylate/sodium acryloyldimethyl taurate) copolymer, and
(C) a water-swelling clay mineral;
(2) The solid powder cosmetic according to the (1), wherein the powder as component (A) contains an amino-modified silicone-treated powder;
(3) The solid powder cosmetic according to the (1) or (2), wherein a content of component (B) is 0.1% to 2% by mass;
(4) The solid powder cosmetic according to any one of the (1) to (3), wherein a content of component (C) is 0.1% to 2% by mass;
(5) The solid powder cosmetic according to any one of the (1) to (4), wherein a content of component (A) is 80% to 99% by mass;
(6) The solid powder cosmetic according to any one of the (1) to (5), further comprising an oily component at a content of 10% by mass or less; and
(7) A method for producing a solid powder cosmetic, comprising:
mixing a cosmetic base containing components (A) to (C):
(A) a powder,
(B) a (sodium acrylate/sodium acryloyldimethyl taurate) copolymer, and
(C) a water-swelling clay mineral,
with a solvent to form a slurry; and
filling a container with the slurry, and then removing the solvent.

Effect of the Invention

The present invention provides a solid powder cosmetic exhibiting excellent ease of loosening of the cosmetic, smooth feeling in use, and adhesiveness to the skin and exhibiting no change in usability in continuous use and having excellent filling and molding properties and drop strength.

MODE OF CARRYING OUT THE INVENTION

The present invention will now be described in detail. Throughout the specification, a numerical range defined with "to" is meant to include the numbers preceding and following the "to."

The powder as the component (A) used in the present invention may be any powder that is commonly used in cosmetics and may have any shape, such as a spherical, plate-like, or acicular shape; any particle diameter, such as an aerosol, fine particle, or pigment grade size; and any particle structure, such as a porous or nonporous structure. Examples of the powder include an inorganic powder, a glitter powder, an organic powder, a colorant powder, and a composite powder. Specifically, examples of the powder include an inorganic powder, such as titanium oxide, black titanium oxide, iron blue, ultramarine, red iron oxide, yellow iron oxide, black iron oxide, zinc oxide, aluminum oxide, silicon dioxide, magnesium oxide, zirconium oxide, magnesium carbonate, calcium carbonate, chromium oxide, chromium hydroxide, carbon black, aluminum silicate, magnesium silicate, mica, synthetic mica, sericite, talc, silicon carbide, barium sulfate, and boron nitride; a glitter powder, such as bismuth oxychloride, mica titanium, iron oxide-coated mica, iron oxide mica titanium, organic pigment-treated mica titanium, a titanium oxide-treated glass powder, and an aluminum powder; an organic powder, such as a nylon powder, polymethyl methacrylate, a polyethylene powder, a polystyrene powder, an organopolysiloxane elastomer powder, a polymethylsilsesquioxane powder, a polyurethane powder, a wool powder, a silk powder, crystalline cellulose, and N-acyl lysine; a colorant powder, such as an organic tar pigment and an organic colorant lake pigment; and a composite powder, such as fine particle titanium oxide-coated mica titanium, fine particle zinc oxide-coated mica titanium, barium sulfate-coated mica titanium, titanium oxide-containing silicon dioxide, and zinc oxide-containing silicon dioxide. One or more of these powders can be used. These powders may be surface-treated with a surface treatment agent, such as a silicone, a fluorine compound, a metal soap, and an oil, by a commonly known method, in order to improve the dispersibility and adhesiveness.

The content of the powder as the component (A) used in the present invention is not particularly limited and is preferably 80% to 99% by mass (hereinafter, simply referred to as %) and further preferably 90% to 99%. This range is more preferable in that within this range, ease of loosening of the cosmetic, smooth feeling in use, and so on are greater.

The powder as the component (A) used in the present invention more preferably contains a powder treated with an amino-modified silicone (hereinafter, referred to as "amino-modified silicone-treated powder"), which improves the affinity of the cosmetic to the skin and also improves the network crosslinking with the polymer containing amino groups of the component (B) (sodium acrylate/sodium acryloyldimethyl taurate) copolymer to provide greater adhesiveness to the skin, smooth feeling in use, and filling and molding properties, drop strength, and so on.

The content of the amino-modified silicone-treated powder in the powder as the component (A) used in the present invention is not particularly limited and is preferably 5% or more, further preferably 10% to 99%, and particularly preferably 20% to 99% based on the total amount of the cosmetic. This range is more preferable in that within this range, the affinity to the skin can be improved, while appropriate hydrophobicity is maintained, to provide greater smooth feeling in use, adhesiveness to the skin, and so on.

The amino-modified silicone used for preparing the amino-modified silicone-treated powder may be any silicone having an amino group or an ammonium group and may be an amino-modified silicone oil in which the whole or a part of the terminal hydroxyl groups are blocked with, for example, methyl groups or may be an amodimethicone in which the terminals are not blocked. For example, preferred examples of the amino-modified silicone include those represented by the following Formula (1):

[Formula 1]

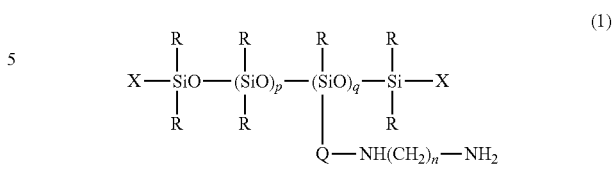

wherein R represents a hydroxyl group, a hydrogen atom, or $R^1$; $R^1$ represents a substituted or unsubstituted monovalent hydrocarbon group having 1 to 20 carbon atoms; X represents $R^1$, $-Q-NH(CH_2)_nNH_2$, $-OR^1$, or a hydroxyl group; Q represents a divalent hydrocarbon group having 1 to 8 carbon atoms; n represents a number of 1 to 5; and p and q represent numbers of which the sum is 2 or more and less than 2000, preferably 20 or more and less than 2000, and further preferably 30 or more and less than 1000 as the number average.

The amino-modified silicone preferably has an amino equivalent of 200 g/mol to 30000 g/mol, further preferably 500 g/mol to 10000 g/mol, and further preferably 600 g/mol to 5000 g/mol.

Herein, the term "amino equivalent" refers to the mass of a siloxane skeleton for one amino group or ammonium group. The unit "g/mol" represents the mass converted into the value for one mole of an amino group or ammonium group. Accordingly, a smaller amino equivalent value denotes a higher ratio of the amino group or ammonium group in the molecule.

The amino-modified silicone preferably has a viscosity within a range of 100 to 3000 mm$^2$/s (25° C.) from the point of view that the powder is uniformly coated and the dispersibility of the powder is improved.

Preferred examples of the commercial product of the above-described amino-modified silicone include an amino-modified silicone oil, such as SF8451C (manufactured by Dow Corning Toray Co., Ltd., viscosity: 600 mm$^2$/s, amino equivalent: 1700 g/mol), SF8452C (manufactured by Dow Corning Toray Co., Ltd., viscosity: 700 mm$^2$/s, amino equivalent: 6400 g/mol), SF8457C (manufactured by Dow Corning Toray Co., Ltd., viscosity: 1200 mm$^2$/s, amino equivalent: 1800 g/mol), KF8003 (manufactured by Shin-Etsu Chemical Co., Ltd., viscosity: 1850 mm$^2$/s, amino equivalent: 2000 g/mol), KF8004 (manufactured by Shin-Etsu Chemical Co., Ltd., viscosity: 800 mm$^2$/s, amino equivalent: 1500 g/mol), KF867S (manufactured by Shin-Etsu Chemical Co., Ltd., viscosity: 1300 mm$^2$/s, amino equivalent: 1700 g/mol), and XF42-B8922 (manufactured by Momentive Performance Materials Inc., viscosity: 70000 mm$^2$/s, amino equivalent: 13000 g/mol); and an amodimethicone emulsion, such as SM8704C (manufactured by Dow Corning Toray Co., Ltd., amino equivalent: 1800 g/mol). Each viscosity is the value at 25° C.

The amino-modified silicone is preferably in a liquid state at 25° C. and may be used in an emulsion form. The amino-modified silicone emulsion can be prepared, for example, by mechanically mixing an amino-modified silicone and a solvent with a high shear force, by emulsifying an amino-modified silicone with water and an emulsifier, by combination of the mechanical mixing and the emulsification, or by emulsion polymerization.

In the preparation of the amino-modified silicone-treated powder, the throughput of the amino-modified silicone is not particularly limited and is preferably 0.1 to 10 parts based on 100 parts by mass (hereinafter, simply referred to as "part (s)") of the powder to be treated, from the viewpoint of providing greater smooth feeling in use, adhesiveness to the skin, and so on, and furthermore, further preferably 0.5 to 7 parts for making such effects significant.

The powder to be surface-treated with an amino-treated modified silicone may be any powder that is commonly used in cosmetics and may have any shape, such as a spherical, plate-like, or acicular shape; any particle diameter, such as an aerosol, fine particle, or pigment grade size; and any particle structure, such as a porous or nonporous structure. Examples of the powder include an inorganic powder, a glitter powder, an organic powder, a colorant powder, and a composite powder.

Specifically, examples of the powder include an inorganic powder, such as titanium oxide, black titanium oxide, cerium oxide, iron blue, ultramarine, red iron oxide, yellow iron oxide, black iron oxide, zinc oxide, aluminum oxide, anhydrous silicic acid, magnesium oxide, zirconium oxide, magnesium carbonate, calcium carbonate, calcium sulfate, chromium oxide, chromium hydroxide, carbon black, aluminum silicate, magnesium silicate, mica, synthetic mica, sericite, talc, silicon carbide, barium sulfate, and boron nitride; a glitter powder, such as bismuth oxychloride, titanium oxide-coated mica, iron oxide-coated mica, iron oxide-coated mica titanium, organic pigment-coated mica titanium, and an aluminum powder; an organic powder, such as a nylon powder, a polymethyl methacrylate powder, an acrylonitrile-methacrylic acid copolymer powder, a vinylidene chloride-methacrylic acid copolymer powder, a polyethylene powder, a polystyrene powder, a (dimethicone/vinyl dimethicone) cross polymer powder, a (vinyl dimethicone/methicone silsesquioxane) cross polymer powder, a (diphenyl dimethicone/vinyl diphenyl dimethicone/silsesquioxane) cross polymer powder, a polymethylsilsesquioxane powder, a polyurethane powder, a wool powder, a silk powder, and N-acyl lysine; a colorant powder, such as an organic tar pigment and an organic colorant lake pigment; and a composite powder, such as fine particle titanium oxide-coated mica titanium, fine particle zinc oxide-coated mica titanium, barium sulfate-coated mica titanium, titanium oxide-containing silica, and zinc oxide-containing silica. One or more of these powders can be used.

Among these powders, from the viewpoint of the effect of improving the network crosslinking with the polymer containing amino groups of the component (B) (the effect of improving the filling and molding properties and the drop strength), inorganic powders, such as titanium oxide, zinc oxide, red iron oxide, yellow iron oxide, black iron oxide, anhydrous silicic acid, calcium carbonate, calcium sulfate, mica, synthetic mica, sericite, talc, and barium sulfate, are preferred. Among them, plate-like powders are preferred. Specifically, for example, mica, synthetic mica, sericite, talc, plate-like barium sulfate, and plate-like calcium sulfate are preferred.

The average particle diameter is preferably 0.5 to 200 µm and more preferably 1 to 150 µm from the viewpoint of powder dispersibility and usability. In the present invention, the term "average particle diameter" refers to an average determined based on the widths and the lengths of powder particles dispersed in water measured with a laser diffraction/scattering particle size distribution analyzer (the average particle diameter at 50% of the cumulative volume).

The amino-modified silicone-treated powder of the present invention can be obtained by dispersing an amino-modified silicone in a solvent and subjecting the powder particle surfaces to coating treatment or by bringing a powder and an amino-modified silicone into contact with each other and subjecting the powder particle surfaces to coating treatment with a mechanical force optionally using, for example, a solvent.

The method for subjecting the powder particle surfaces to coating treatment with an amino-modified silicone is not particularly limited, and a commonly known method is used. Specifically, for example, a method for directly mixing an amino-modified silicone with a powder, or a method for using an amino-modified silicone dissolved in a solvent, such as water, ethanol, isopropyl alcohol, n-hexane, light isoparaffin, benzene, and toluene, is used. In addition, a gas phase method and a mechanochemical method can be used. The mechanochemical method preferably uses a kneader having a mechanism capable of applying a shear force in a shear-driven pressurized state, such as a mortar machine (raikai mixer), a pressure kneader, a mixmuller, a roll mill, a Banbury mixer, and a millstone.

In a particularly preferred aspect, a shearing type low-speed kneader is used. For example, an amino-modified silicone, a powder, and a solvent are mixed with, for example, a mortar machine, the mixture is heated to 70° C. to 120° C., and crushing is then performed.

In another preferred aspect, an amino-modified silicone is dissolved in a solvent and is then mixed with a powder. The solvent is removed by drying or is removed by drying with heating to 70° C. to 120° C., followed by crushing. Among these aspects, particularly preferred is an amino-modified silicone-coated powder prepared by mixing an amino-modified silicone and a powder with a shearing type low-speed kneader, then heating the mixture to 70° C. to 120° C., and performing crushing.

It is preferable to heat the powder coated with an amino-modified silicone to about 70° C. to 120° C. as described above, because the amino group and the oxygen atom of a siloxane bond in the amino-modified silicone more strongly interact with the powder particle surface to improve the water repellency, light extendability, and makeup-lasting quality over time. It is also preferable, because kneading with a solvent scratches the surface of the base with strong friction during the kneading, and the amino-modified silicone can electrostatically adsorb to the newly exposed active site to improve the coating of the powder particle surfaces, leading to improvements in not only the filling and molding properties and the drop strength but also the smooth feeling in use and the adhesiveness to the skin.

Examples of the commercial product of the above-described amino-modified silicone-treated powder include "Mica Y-2300WA3" (manufactured by Yamaguchi Mica Co., Ltd., average particle diameter: 19 µm), which is mica as a powder is treated with an amino-modified silicone, and "EX-15WA3" (manufactured by Yamaguchi Mica Co., Ltd., average particle diameter: 15 µm), which is talc treated with an amino-modified silicone.

The component (B) (sodium acrylate/sodium acryloyldimethyl taurate) copolymer used in the present invention is a copolymer of sodium acrylate and sodium acryloyldimethyl taurate and corresponds to the material described as "sodium acrylate/sodium acryloyldimethyl taurate copolymer" in The International Cosmetic Ingredient Dictionary. The copolymer may be used alone or as a composition containing another component. Examples of the commercial product of the copolymer include SIMULGEL (registered trademark) EG (manufactured by SEPPIC) which is an aqueous dispersion containing 37.5% of the copolymer.

The content of the component (B) in the present invention is not particularly limited and is preferably 0.1% to 2% and more preferably 0.3% to 1%. This range is more preferable in that within this range, smooth feeling in use, no change in usability in continuous use, drop strength, and so on are greater.

The component (C) water-swelling clay mineral used in the present invention is a clay mineral that swells when dispersed in water. Specifically, examples of the clay mineral include, but not limited to, bentonite, smectite, montmorillonite, beadelite, nontrite, and hectorite. One or more of these clay minerals can be used. Among them, the component (C) more preferably contains bentonite, smectite, or hectorite from the viewpoint of providing greater ease of loosening of the cosmetic, drop strength, and so on, and further preferably contains smectite from the viewpoint of further improving the drop strength. Examples of the commercial product of the clay mineral include Kunipia (registered trademark) G-4 (manufactured by Kunimine Industries Co., Ltd.), Lucentite (registered trademark) SWN (manufactured by Co-op Chemical Co., Ltd.), Bengel (registered trademark) (manufactured by Hojun Co., Ltd.), and Sumecton (registered trademark) SA-2 (manufactured by Kunimine Industries Co., Ltd.).

The content of the component (C) in the present invention is not particularly limited and is preferably 0.1% to 2% and more preferably 0.3% to 1%. This range is more preferable in that within this range, ease of loosening of the cosmetic, drop strength, and so on are greater.

The solid powder cosmetic of the present invention can comprise components that are commonly used in cosmetics, in addition to the components (A) to (C), within a range that does not impair the effects of the present invention. For example, the solid powder cosmetic can appropriately contain an oily component, a surfactant, an ultraviolet absorber, an aqueous component, a moisturizing agent, a fading inhibitor, an antioxidant, a beauty component, a preservative, and a fragrance within a range that does not impair the effects of the present invention.

The oily component is not particularly limited, as long as the oil is an oil that is commonly used in cosmetics and, for example, it may have any origin, such as animal oil, vegetable oil, and synthetic oil, and any property, such as solid oil, semisolid oil, and liquid oil. Examples of the oily component include a hydrocarbon, fat and oil, a wax, a hydrogenated oil, an ester oil, a fatty acid, a higher alcohol, a silicone oil, a fluorine-based oil, a lanolin derivative, an oil gelling agent, and an oil-soluble resin.

Specifically, examples of the oily component include a volatile oil, for example, a hydrocarbon, such as liquid paraffin, squalane, Vaseline, paraffin wax, ceresin wax, microcrystalline wax, an ethylene propylene copolymer, montan wax, and Fischer-Tropsch wax; fat and oil, such as Japan wax, olive oil, castor oil, mink oil, and macadamia nut oil; a wax, such as beeswax, carnauba wax, candelilla wax, and spermaceti; an ester, such as Jojoba oil, cetyl octanoate, isopropyl myristate, isopropyl palmitate, octyldodecyl myristate, glyceryl trioctanoate, polyglyceryl diisostearate, diglyceryl triisostearate, glyceryl tribehenate, diisostearyl malate, neopentyl glycol dioctanoate, cholesterol fatty acid ester, and di(cholesteryl/behenyl/octyldodecyl) N-lauroyl-L-glutamate; a higher alcohol, such as stearyl alcohol, cetyl alcohol, lauryl alcohol, oleyl alcohol, isostearyl alcohol, and behenyl alcohol; a silicone, such as methylphenyl polysiloxane and fluorine-modified organopolysiloxane; a fluorine-based oil, such as perfluorodecane, perfluorooctane, and perfluoropolyether; a lanolin derivative, such as lanolin, lanolin acetate, isopropyl lanolin fatty acid, and lanolin alcohol; an oil gelling agent, such as dextrin octanoate, dextrin laurate, dextrin palmitate, dextrin myristate, dextrin stearate, dextrin behenate, a dextrin coconut oil fatty acid ester, dextrin (palmitate/octanoate), a sucrose fatty acid ester, a starch fatty acid ester, 12-hydroxystearic acid, and calcium stearate; an oil-soluble resin, such as hydrogenated pentaerythrityl rosinate and a specific alkyl acrylate methylpolysiloxane ester; a hydrocarbon oil, such as light liquid isoparaffin and isododecane; and a silicone, such as decamethylcyclopentasiloxane, octamethylcyclotetrasiloxane, methyl trimethicone, and dimethylpolysiloxane having a low degree of polymerization. One or more of these oily components can be used.

The content of the oily component in the present invention is preferably 10% or less and further preferably 5% or less from the viewpoint of smooth feeling in use and adhesiveness to the skin.

Examples of the surfactant include a nonionic surfactant, such as a glycerin fatty acid ester and its alkylene glycol adduct, a polyglycerin fatty acid ester and its alkylene glycol adduct, a propylene glycol fatty acid ester and its alkylene glycol adduct, a sorbitan fatty acid ester and its alkylene glycol adduct, a sorbitol fatty acid ester and its alkylene glycol adduct, a polyalkylene glycol fatty acid ester, a polyoxyalkylene-modified silicone, and polyoxyalkylene-alkyl-co-modified silicone; an anionic surfactant, such as a fatty acid (e.g., stearic acid and lauric acid) and its inorganic or organic salt, an alkyl benzene sulfate, an alkyl sulfonate, an α-olefin sulfonate, a dialkyl sulfosuccinate, an α-sulfonated fatty acid salt, an acyl methyl taurine salt, an N-methyl-N-alkyl taurine salt, a polyoxyethylene alkyl ether sulfate, a polyoxyethylene alkyl phenyl ether sulfate, an alkyl phosphate, a polyoxyethylene alkyl ether phosphate, a polyoxyethylene alkyl phenyl ether phosphate, and an N-acyl-N-alkyl amino acid salt; a cationic surfactant, such as an alkylamine salt, a polyamine or alkanolamine fatty acid derivative, an alkyl ammonium salt, and an alicyclic ammonium salt; and an amphoteric surfactant, such as a phospholipid and N,N-dimethyl-N-alkyl-N-carboxymethylammonium betaine. One or more of these surfactants can be used.

The ultraviolet absorber may be any ultraviolet absorber that is commonly used in cosmetics, and examples thereof include a benzophenone-based ultraviolet absorber, such as 2-hydroxy-4-methoxybenzophenone, 2-hydroxy-4-methoxybenzophenone-5-sulfonic acid, sodium 2-hydroxy-4-methoxybenzophenone-5-sulfonate, 2,2'-dihydroxy-4,4'-dimethoxybenzophenone, sodium 2,2'-dihydroxy-4,4'-dimethoxybenzophenone-5-sulfonate, 2,4-dihydroxybenzophenone, 2,2',4,4'-tetrahydroxybenzophenone, 2,4,6-trianilino-para-(carbo-2'-ethylhexyl-1'-oxy)-1,3,5-triazine, 2,4-bis[{4-(2-ethylhexyloxy)-2-hydroxy}-phenyl]-6-(4-methoxyphenyl)-(1,3,5)-triazine, and 2-2'-methylene-bis-{6-(2H-benzotriazol-2-yl)-4-(1,1,3,3-tetramethylbutyl)phenol}; a PABA-based ultraviolet absorber, such as p-aminobenzoic acid, ethyl p-aminobenzoate, glyceryl p-aminobenzoate, amyl p-dimethylaminobenzoate, 2-ethylhexyl p-dimethylaminobenzoate, ethyl p-dihydroxypropylbenzoate, and hexyl 2-{4-(diethylamino)-2-hydroxybenzoyl}benzoate; a cinnamic acid-based ultraviolet absorber, such as 2-ethylhexyl p-methoxycinnamate and 2-ethoxyethyl 4-methoxycinnamate; a salicylic acid-based ultraviolet absorber, such as 2-ethylhexyl salicylate, phenyl salicylate, and homomenthyl salicylate; a dibenzoylmethane-based ultraviolet absorber, such as 4-tert-4'-methoxydibenzoylmethane; and 2-2'-methylene-bis-{6-(2H-benzotriazol-2-yl)-4-(1,1,3,3-tetramethylbutyl)phenol}. One or more of these ultraviolet absorbers can be used.

The aqueous component other than the component (B) may be water or any water-soluble component, for example, a lower alcohol, such as ethyl alcohol and propyl alcohol; a glycol, such as propylene glycol, 1,3-butylene glycol, dipropylene glycol, 1,2-pentanediol, and polyethylene glycol; a glycerol, such as glycerin, diglycerin, and polyglycerin; a plant extract, such as aloe vera, witch hazel, hamamelis, cucumber, lemon, lavender, and rose; and a water-soluble polymer, for example, a cellulose derivative, such as methylcellulose, hydroxymethylcellulose, hydroxyethylcellulose, hydroxypropylcellulose, hydroxypropylmethylcellulose, and carboxymethylcellulose; a natural polymer, such as sodium alginate, carrageenan, quince seed gum, agar, gelatin, xanthan gum, locust bean gum, pectin, and gellan gum; and a synthetic polymer, such as polyvinyl alcohol, a carboxyvinyl polymer, an alkyl addition carboxyvinyl polymer, sodium polyacrylate, sodium polymethacrylate, polyacrylic acid glycerin ester, and polyvinylpyrrolidone. One or more of these aqueous components can be used.

Examples of the moisturizing agent include a protein, a mucopolysaccharide, a collagen, elastin, and keratin. Examples of the antioxidant include α-tocopherol and ascorbic acid. Examples of the beauty component include a vitamin, an anti-inflammatory agent, and an herbal medicine. Examples of the preservative include paraoxybenzoic acid ester, 1,3-butylene glycol, 1,2-pentanediol, and phenoxyethanol.

The method for producing solid powder cosmetic of the present invention is not particularly limited and the solid powder cosmetic of the present invention can be produced according to a conventionally known method. For example, the solid powder cosmetic can be produced by a dry press method involving filling a container, such as a metal plate, with a cosmetic in powder form and then pressing the cosmetic or by a wet filling method involving adding a solvent, such as a volatile compound, to a composition prepared by mixing the above-mentioned components to form a slurry, filling a container, such as a metal plate, with the slurry, and applying a pressure to the slurry to remove a part of the solvent, and further completely removing the solvent.

Although the filling method may be the dry press method or the wet filling method, more preferred is the wet filling method involving mixing a cosmetic base containing the components (A) to (C) with a solvent to form a slurry, filling a container with the slurry, and then removing the solvent, from the viewpoint of providing greater drop strength and so on through uniform dispersion of the components (A) to (C).

The solvent to be used in the wet filling method is preferably a volatile compound having a boiling point of 260° C. or less at normal pressure. Examples of the solvent include water; a low boiling-point alcohol, such as ethyl alcohol, isopropyl alcohol, and n-butanol; a low boiling-point hydrocarbon oil, such as isododecane, isohexadecane, and light liquid isoparaffin; a linear or cyclic silicone oil having a low boiling-point point, such as dimethylpolysiloxane, methyl trimethicone, octamethyl cyclotetrasiloxane, and decamethyl cyclopentasiloxane each having a low degree of polymerization; and a low boiling-point fluorine compound, such as a low boiling-point perfluoropolyether. These solvents are used alone or as a mixture of two or more thereof. Alternatively, an emulsion prepared by dispersing the oily components of a cosmetic base in water can be used.

The amount of the solvent mixed in the present invention is appropriately determined so that the mixture before molding can have fluidity for filling a container or an inner plate with the mixture, and is preferably 10 to 200 parts based on 100 parts of the cosmetic base. Within this range, the solvent can be satisfactorily removed.

In the present invention, the term "fluidity" means a state in which when a container having an aperture diameter of 2.47 cm, a barrel diameter of 4.05 cm, and a height of 7.4 cm ("Medicine Bottle PS-6K", manufactured by Daiichi Glass), being filled with 30 g of a mixture prepared by mixing a cosmetic base mainly composed of powder with a solvent, and being closed with an attached lid is slanted by 90° and left to stand at 25° C. under an environment of 1 atm for 1 minute, a part of the mixture adheres to the inner side of the lid.

In the method of preparing the solid powder cosmetic of the present invention, the method for removing the solvent is not particularly limited, and a commonly known method can be used. It is preferable to adopt a method for removing a solvent with an absorber or through a discharge hole by directly drying or by applying a pressure to a mixture of a cosmetic base and the solvent after filling. For example, it is preferred to weakly press the mixture of the cosmetic base and the solvent with, for example, a pad when a container or an inner plate is filled with the mixture, for smoothening the surface. It is also possible to absorb the solvent with a porous press head or an absorber during the pressing. Alternatively, the solvent can be removed by drying, and the conditions therefor are appropriately set depending on the boiling point and the specific heat of the solvent. For example, in the case of light liquid isoparaffin, drying is performed at 50° C. to 70° C. for about 10 to 20 hours.

The solid powder cosmetic of the present invention can be applied to, for example, makeup cosmetics and skin care cosmetics and can be formed into a product form by being molded into a variety of shapes depending on the purpose. Examples of the shape include a wide variety of shapes, such as dome, hemispherical, conical, pyramid, and diamond cut shapes and a shape having a surface provided with asperities showing a brand logo or various patterns. Examples of the product form include foundation, blusher, eyeshadow, eyeliner, eyebrow, face powder, and body powder. In particularly, it is more preferable from the viewpoint of exhibiting more effects of providing excellent ease of loosening of the cosmetic, smooth feeling in use, and adhesiveness to the skin in makeup cosmetics, such as foundation, blusher, eyeshadow, and face powder.

EXAMPLES

The present invention will now be described in further detail with reference to production examples of an amino-modified silicone-treated powder and Examples of the present invention, which do not limit the present invention.

Production Example 1

Production of Amino-Modified Silicone-Treated Titanium Oxide

Five parts of an amino-modified silicone (KF8003, manufactured by Shin-Etsu Chemical Co., Ltd.) was dissolved in 70 parts of isopropyl alcohol, and 95 parts of titanium oxide (CR-50: manufactured by Ishihara Sangyo Kaisha, Ltd., average particle diameter: 0.25 μm) was added to the solution. The resulting mixture was mixed with a super mixer (SMP-2, manufactured by Kawata Mfg. Co., Ltd.), and the isopropyl alcohol was then removed by evaporative drying at 80° C. The resulting dry material was crushed with an atomizer (LM-05, manufactured by Dalton Corp.) to give an amino-modified silicone-treated titanium oxide (5% treatment) in powder form.

Production Example 2

Production of Amino-Modified Silicone-Treated Mica [1]
Three parts of an amino-modified silicone (KF867S, manufactured by Shin-Etsu Chemical Co., Ltd.), 97 parts of mica (Y-2300, manufactured by Yamaguchi Mica Co., Ltd., average particle diameter: 19 μm), and 10 parts of water were mixed with a mortar machine (ZOD model, manufactured by Ishikawa Kojo Co., Ltd.) for 3 hours and heated at 100° C. for 4 hours. The resulting material was then crushed with an atomizer (LM-05, manufactured by Dalton Corp.) to give an amino-modified silicone-treated mica (3% treatment) in powder form.

Production Example 3

Production of Amino-Modified Silicone-Treated Mica [2]
One part of an amino-modified silicone (KF867S, manufactured by Shin-Etsu Chemical Co., Ltd.), 99 parts of mica (Y-2300, manufactured by Yamaguchi Mica Co., Ltd., average particle diameter: 19 μm), and 10 parts of water were mixed with a mortar machine (ZOD model, manufactured by Ishikawa Kojo Co., Ltd.) for 3 hours and heated at 100° C. for 4 hours. The resulting material was then crushed with an atomizer (LM-05, manufactured by Dalton Corp.) to give an amino-modified silicone-treated mica (1% treatment) in powder form.

Production Example 4

Production of Amino-Modified Silicone-Treated Mica [3]
One part of amino-modified silicone (KF867S, manufactured by Shin-Etsu Chemical Co., Ltd.), 99 parts of mica (SA-350, manufactured by Yamaguchi Mica Co., Ltd., average particle diameter: 42 μm), and 10 parts of water were mixed with a mortar machine (ZOD model, manufactured by Ishikawa Kojo Co., Ltd.) for 3 hours and heated at 100° C. for 4 hours. The resulting material was then crushed with an atomizer (LM-05, manufactured by Dalton Corp.) to give an amino-modified silicone-treated mica (1% treatment) in powder form.

Production Example 5

Production of Amino-Modified Silicone-Treated Talc [1]
Three parts of an amino-modified silicone (KF8004, manufactured by Shin-Etsu Chemical Co., Ltd.), 97 parts of talc (EX-15, manufactured by Yamaguchi Mica Co., Ltd., average particle diameter: 15 μm), and 10 parts of water were mixed with a mortar machine for 3 hours and heated at 90° C. for 3 hours. The resulting material was then crushed with an atomizer (LM-05, manufactured by Dalton Corp.) to give an amino-modified silicone-treated talc (3% treatment) in powder form.

Production Example 6

Production of Amino-Modified Silicone-Treated Talc [2]
Two parts of an amino-modified silicone (SF8451C, manufactured by Dow Corning Toray Co., Ltd.) and 98 parts of talc (JA-13R, manufactured by Asada Milling Co., Ltd., average particle diameter: 6 μm) were mixed with a super mixer for 10 minutes and heated at 70° C. for 5 hours. The resulting material was then crushed with an atomizer (LM-05, manufactured by Dalton Corp.) to give an amino-modified silicone-treated talc (2% treatment) in powder form.

Examples 1 to 12 and Comparative Examples 1 to 5

Eye Shadow
Eyeshadows shown in Table 1 were prepared and were evaluated for the filling and molding properties, drop strength, no change in usability in continuous use, ease of loosening of the cosmetic, smooth feeling in use, adhesiveness to the skin and were rated according to the rating criteria shown below. The results are also shown in Table 1.

TABLE 1

| No. | Component | Example 1 | 2 | 3 | 4 | 5 | 6 | 7 | 8 | 9 |
|---|---|---|---|---|---|---|---|---|---|---|
| 1 | Amino-modified silicone-treated mica (particle diameter: 19 μm) *1 | 65 | 10 | 65 | — | — | — | — | 55 | 65 |
| 2 | Amino-modified silicone-treated mica [2] of Production Example 3 | — | — | — | 65 | — | — | — | — | — |
| 3 | Amino-modified silicone-treated mica [3] of Production Example 4 | — | — | — | — | 65 | — | — | — | — |
| 4 | Mica (particle diameter: 19 μm) *2 | Balance | Balance | Balance | Balance | Balance | Balance | Balance | Balance | Balance |
| 5 | Mica (particle diameter: 42 μm) *3 | — | — | — | — | — | — | 65 | — | — |
| 6 | Titanium oxide | 0.3 | 0.3 | 0.3 | 0.3 | 0.3 | 0.3 | 0.3 | 0.3 | 0.3 |
| 7 | Black iron oxide | 0.1 | 0.1 | 0.1 | 0.1 | 0.1 | 0.1 | 0.1 | 0.1 | 0.1 |
| 8 | Red iron oxide | 0.2 | 0.2 | 0.2 | 0.2 | 0.2 | 0.2 | 0.2 | 0.2 | 0.2 |
| 9 | Yellow iron oxide | 0.2 | 0.2 | 0.2 | 0.2 | 0.2 | 0.2 | 0.2 | 0.2 | 0.2 |

TABLE 1-continued

| No. | Component | | | | | | | | | |
|---|---|---|---|---|---|---|---|---|---|---|
| 10 | Mica titanium *4 | 5 | 5 | 5 | 5 | 5 | 5 | 5 | 5 | 5 |
| 11 | Titanium oxide-treated glass powder *5 | 5 | 5 | 5 | 5 | 5 | 5 | 5 | 5 | 5 |
| 12 | Methyl methacrylate cross polymer *6 | 13 | 13 | 13 | 13 | 13 | 13 | 13 | 13 | 13 |
| 13 | (Sodium acrylate/sodium acryloyldimethyl taurate) copolymer *7 | 1 | 1 | 1 | 1 | 1 | 1 | 1 | 3 | 1 |
| 14 | Xanthan gum | — | — | — | — | — | — | — | — | — |
| 15 | (Acrylic acid/(C10-30) alkyl acrylate) copolymer *8 | — | — | — | — | — | — | — | — | — |
| 16 | Magnesium aluminum silicate *9 | 1 | 1 | 1 | 1 | 1 | 1 | 1 | 2 | — |
| 17 | Hydrated aluminum silicate *10 | — | — | — | — | — | — | — | — | 1 |
| 18 | Silica *11 | — | — | — | — | — | — | — | — | — |
| 19 | Cetyl 2-ethylhexanoate *12 | 5 | 5 | — | 5 | 5 | 5 | 5 | 10 | 5 |

<Evaluation item and evaluation>

| | | | | | | | | | | |
|---|---|---|---|---|---|---|---|---|---|---|
| I | Filling and molding properties | Excellent | Excellent | Excellent | Excellent | Excellent | Good | Good | Good | Excellent |
| II | Drop strength | Excellent | Excellent | Good | Good | Good | Good | Good | Excellent | Excellent |
| III | No change in usability in continuous use | Excellent | Excellent | Excellent | Excellent | Excellent | Excellent | Excellent | Good | Excellent |
| IV | Ease of loosening of cosmetic | Excellent | Excellent | Excellent | Excellent | Excellent | Good | Good | Good | Good |
| V | Smooth feeling in use | Excellent | Good | Excellent | Excellent | Excellent | Good | Good | Good | Excellent |
| VI | Adhesiveness to the skin | Excellent | Good | Excellent | Excellent | Excellent | Good | Good | Excellent | Excellent |

| | | Example | | | Comparative Example | | | | |
|---|---|---|---|---|---|---|---|---|---|
| No. | Component | 10 | 11 | 12 | 1 | 2 | 3 | 4 | 5 |
| 1 | Amino-modified silicone-treated mica (particle diameter: 19 μm) *1 | 65 | 65 | 30 | 65 | 65 | 65 | 65 | 65 |
| 2 | Amino-modified silicone-treated mica [2] of Production Example 3 | — | — | — | — | — | — | — | — |
| 3 | Amino-modified silicone-treated mica [3] of Production Example 4 | — | — | — | — | — | — | — | — |
| 4 | Mica (particle diameter: 19 μm) *2 | Balance | Balance | Balance | Balance | Balance | Balance | Balance | Balance |
| 5 | Mica (particle diameter: 42 μm) *3 | — | — | — | — | — | — | — | — |
| 6 | Titanium oxide | 0.3 | 0.3 | 0.3 | 0.3 | 0.3 | 0.3 | 0.3 | 0.3 |
| 7 | Black iron oxide | 0.1 | 0.1 | 0.1 | 0.1 | 0.1 | 0.1 | 0.1 | 0.1 |
| 8 | Red iron oxide | 0.2 | 0.2 | 0.2 | 0.2 | 0.2 | 0.2 | 0.2 | 0.2 |
| 9 | Yellow iron oxide | 0.2 | 0.2 | 0.2 | 0.2 | 0.2 | 0.2 | 0.2 | 0.2 |
| 10 | Mica titanium *4 | 5 | 5 | 5 | 5 | 5 | 5 | 5 | 5 |
| 11 | Titanium oxide-treated glass powder *5 | 5 | 5 | 5 | 5 | 5 | 5 | 5 | 5 |
| 12 | Methyl methacrylate cross polymer *6 | 13 | 13 | 13 | 13 | 13 | 13 | 13 | 13 |
| 13 | (Sodium acrylate/sodium | 0.5 | 1 | 1 | — | 1 | — | — | 1 |

TABLE 1-continued

| | | | | | | | | | |
|---|---|---|---|---|---|---|---|---|---|
| 14 | Xanthan gum | — | — | — | — | — | 0.4 | — | — |
| 15 | (Acrylic acid/(C10-30) alkyl acrylate) copolymer *8 | — | — | — | — | — | — | 0.8 | — |
| 16 | Magnesium aluminum silicate *9 | 1 | 0.3 | 1 | 1 | — | 1 | 1 | — |
| 17 | Hydrated aluminum silicate *10 | — | — | — | — | — | — | — | — |
| 18 | Silica *11 | — | — | — | — | — | — | — | 1 |
| 19 | Cetyl 2-ethylhexanoate *12 | 5 | 5 | 5 | 5 | 5 | 5 | 5 | 5 |
| <Evaluation item and evaluation> | | | | | | | | | |
| I | Filling and molding properties | Excellent | Excellent | Excellent | Good | Fair | Fair | Poor | Poor |
| II | Drop strength | Good | Good | Excellent | Poor | Poor | Good | Good | Fair |
| III | No change in usability in continuous use | Excellent | Good | Excellent | Good | Good | Poor | Poor | Fair |
| IV | Ease of loosening of cosmetic | Excellent | Good | Excellent | Good | Good | Poor | Poor | Poor |
| V | Smooth feeling in use | Excellent | Excellent | Good | Fair | Good | Fair | Fair | Poor |
| VI | Adhesiveness to the skin | Good | Excellent | Excellent | Fair | Good | Good | Poor | Good |

*1: Mica Y-2300WA3 (manufactured by Yamaguchi Mica Co., Ltd.)
*2: Y-2300 (manufactured by Yamaguchi Mica Co., Ltd.)
*3: SA-350 (manufactured by Yamaguchi Mica Co., Ltd.)
*4: FLAMENCO ORANGE (manufactured by BASF SE), treaded with 2% methyl hydrogen polysiloxane
*5: Microglas Metashine (registered trademark) MT1080RS (manufactured by Nippon Sheet Glass Co., Ltd.)
*6: Matsumoto Microsphere (registered trademark) M-305 (manufactured by Matsumoto Yushi-Seiyaku Co., Ltd.)
*7: SIMULGEL (registered trademark) EG (manufactured by SEPPIC, solid content: 37.5%)
*8: Yodosol (registered trademark) GH-800F (manufactured by Akzo Nobel N. V., solid content: 45%)
*9: Sumecton (registered trademark) SA-2 (manufactured by Kunimine Industries Co., Ltd.)
*10: Kunipia (registered trademark) G-4 (manufactured by Kunimine Industries Co., Ltd.)
*11: AEROSIL (registered trademark) 300 (manufactured by Nippon Aerosil Co., Ltd.)
*12: CETIOL (registered trademark) SN-1 (manufactured by BASF SE)

(Production Method)

A. Components (1) to (12) were uniformly mixed.

B. A uniform mixture of components (13) to (19) was added to the mixture prepared in the step A, followed by uniform dispersion and crushing to give a cosmetic base.

C. A hundred parts of purified water was added to 100 parts of the cosmetic base to give a mixture. The mixture was kneaded at normal temperature and was then packed in a resin plate container having a length of 3 cm, a width of 3 cm, and a height of 0.5 cm. A part of the purified water was collected with an absorber, such as a porous press head, while compressing the mixture. The mixture was then dried at room temperature for a whole day and night to remove the purified water to give an eyeshadow (solid).

(Evaluation Method)

The following evaluation items were evaluated by the methods shown below, respectively.

(Evaluation Item)

I. Filling and molding properties
II. Drop strength
III. No change in usability in continuous use
IV. Ease of loosening of cosmetic
V. Smooth feeling in use
VI. Adhesiveness to the skin Regarding the evaluation item I. Filling and molding properties, five samples were prepared for each eyeshadow and were visually observed to evaluate the moldability and evaluated and scored on a 5-point scale with the following absolute evaluation. The average of the scores for the five samples was calculated from the sum of the scores of n=5, and each eyeshadow was rated according to the four-rating criteria shown below.

Regarding the evaluation criteria, if the solvent is difficult to be removed during molding, the surface peels immediately after the molding to prevent three-dimensional molding; defects, such as cracking and peeling, occur on the surface of the cosmetic after drying; or even if no defect occurs, undesired asperities or unevenness is observed on the surface of the cosmetic. In contrast, if the solvent is easily removed, three-dimensional molding is possible; defects, such as cracking and peeling, do not occur on the surface of the cosmetic even after drying; and a cosmetic having a surface free from unintended asperities and unevenness can be prepared.

Accordingly, herein, the filling and molding properties of each cosmetic were evaluated by observing the surface at the time of three-dimensional molding and after drying for cracking, peeling, asperity, and unevenness.

<Absolute Evaluation Criteria>

(Score): (Determination)

5: Three-dimensional molding is possible, and the surface does not have any defect and unintended asperities and unevenness, 4: Three-dimensional molding is possible, and the surface does not have any defect but slightly has unintended asperities or unevenness that does not cause any problem in use, 3: Three-dimensional molding is possible, and the surface does not have any defect but has unintended asperities or unevenness, 2: Three-dimensional molding is possible, but cracking or peeling occurs after drying, and 1: Three-dimensional molding is impossible.

<Four-Rating Criteria>
(Rating): (Average of scores)
Excellent: 4.0 or more: very good,
Good: 3.5 or more and less than 4.0: good,
Fair: 2.0 or more and less than 3.5: slightly poor, and
Poor: less than 2.0: poor.

Regarding the evaluation item II. Drop strength, five samples packed in a resin plate container having a length of 3 cm, a width of 3 cm, and a height of 0.5 cm were prepared for each of the eyeshadows of Examples and Comparative Examples and were each dropped from a height of 50 cm onto an acrylic plate by free fall in the erecting direction. The surface conditions after the dropping were observed and were scored for each eyeshadow according to the evaluation criteria shown below. The average of the scores for the five samples was calculated, and each eyeshadow was rated according to the four-rating criteria shown below.

<Evaluation Criteria (Drop Strength)>
(Score): (Evaluation criteria)
4: No change occurs,
3: Slight twist, cracking, or floating occurs, but it does not cause any problem,
2: Twist, cracking, or floating occurs to cause a problem, and
1: Significant twist, cracking, or floating occurs to cause a problem.

<Rating Criteria>
(Rating): (Average of scores of n=5)
Excellent: 3.5 or more,
Good: 3.0 or more and less than 3.5,
Fair: 2.0 or more and less than 3.0, and
Poor: less than 2.0.

Regarding the evaluation item III. No change in usability in continuous use, the weight ratio of the amounts of each of the eyeshadows of Examples and Comparative Examples taken with a small tool (chip) at the time of starting use and after continuous use was evaluated. Specifically, the decrease in the weight of a filled product when an expert panelist used the product with a chip at a constant strength for 20 times was defined as (A). The panelist further continuously used the filled product 200 times (220 times in total). The weight obtained by subtracting the weight of the filled product continuously used 240 times from the weight of the filled product continuously used 220 times was defined as (B). The usability in continuous use was evaluated based on the weight ratio of (A) to (B). The same evaluation was performed for five samples of each of the eyeshadows of Examples and Comparative Examples. Each eyeshadow was scored according to the evaluation criteria shown below, and the average of the scores for the five samples was calculated, and the eyeshadows were rated according to the four-rating criteria shown below.

(The weight of a filled product before use)−(the weight of the filled product after used 20 times) =(A)

(The weight of the filled product after used 220 times)−(the weight of the filled product after used 240 times)=(B)

<Evaluation Criteria (No Change in Usability in Continuous Use)>
(Score): (Evaluation criteria)
4: the ratio (A)/(B) is 0.8 or more and 1.25 or less,
3: the ratio (A)/(B) is 0.6 or more and less than 0.8 or more than 1.25 and 1.66 or less,
2: the (A)/(B) is 0.1 or more and less than 0.6 or more than 1.66 and 10 or less, and
1: the ratio (A)/(B) is less than 0.1 or more than 10.

<Rating Criteria>
(Rating): (Average of scores of n=5)
Excellent: 3.5 or more,
Good: 3.0 or more and less than 3.5,
Fair: 2.0 or more and less than 3.0, and
Poor: less than 2.0.

Regarding the evaluation items IV to VI, each sample was subjected to use tests by 20 expert panelists.

Each of the eyeshadows of Examples and Comparative Examples was applied to each panelist and was scored on a 5-point scale with the following absolute evaluation. The average of the scores given by the 20 panelists for each sample was calculated and was rated according to the four-rating criteria shown below.

Regarding IV. Ease of loosening, each sample was taken with a finger or a small tool, and it was evaluated whether the amount of the sample adhered to the finger or the small tool was appropriate without being too large or too small. Regarding V. Smooth feeling in use, each sample was applied to the skin, and it was evaluated whether the sample well spread on the skin with sliding feeling and without friction feeling. Regarding VI. Adhesiveness to the skin, each sample was applied to the skin, and it was evaluated whether the cosmetic tightly adhered to the skin without causing powder scattering on the skin.

<Evaluation Criteria>
(Score): (Evaluation)
5: very good,
4: good,
3: moderate,
2: poor, and
1: very poor.

<Four-Rating Criteria>
(Rating): (Average of scores)
Excellent: 4.0 or more: very good,
Good: 3.5 or more and less than 4.0: good,
Fair: 2.0 or more and less than 3.5: slightly poor, and
Poor: less than 2.0: poor.

As obvious from the results shown in Table 1, the eyeshadows of Examples 1 to 12 were excellent in all items: filling and molding properties, drop strength, no change in usability in continuous use, ease of loosening of the cosmetic, smooth feeling in use, and adhesiveness to the skin.

In contrast, in Comparative Example 1 where the component (B) (sodium acrylate/sodium acryloyldimethyl taurate) copolymer was not contained and Comparative Example 2 where the component (C) water-swelling clay mineral was not contained, the drop strength was poor.

In Comparative Example 3 where xanthan gum was contained instead of the component (B) (sodium acrylate/sodium acryloyldimethyl taurate) copolymer, the filling and molding properties were poor and only the surface was hardened after drying, resulting in low loosening of the bulk, poor usability in continuous use, and no smooth feeling in use.

In Comparative Example 4 where a (acrylic acid/(C10-30) alkyl acrylate) copolymer was contained instead of the component (B) (sodium acrylate/sodium acryloyldimethyl taurate) copolymer, the solvent was difficult to be removed during filling, resulting in poor filling and molding properties.

In Comparative Example 5 where aerosol silica was contained instead of the component (C) magnesium aluminum silicate, the filling and molding properties were poor, and low change in usability in continuous use, poor loosening of the cosmetic, and no smooth feeling in use were exhibited.

Example 13: Eyebrow (Solid)

(Component): (%)
1. Black iron oxide: 15
2. Red iron oxide: 5
3. Yellow iron oxide: 8
4. Titanium oxide: 5
5. Amino-modified silicone-treated mica [1] of Production Example 2: 20
6. Mica *2: balance
7. Amino-modified silicone-treated talc [1] of Production Example 5: 5
8. Black iron oxide-coated mica titanium *13: 15
9. Diglyceryl triisostearate: 5
10. Squalane: 1
11. Dimethylpolysiloxane (20 mm$^2$/s at 25° C.): 1
12. Heavy liquid isoparaffin: 1
13. (Sodium acrylate/sodium acryloyldimethyl taurate) copolymer *7: 2
14. Magnesium aluminum silicate *9: 2
*13: COLORONA MICA BLACK (manufactured by Merck KGaA)
(Production Method)
A. Components (1) to (8) were uniformly mixed.
B. A uniform mixture of components (9) to (14) was added to the mixture prepared in the step A, followed by uniform dispersion and crushing to give a cosmetic base.
C. Thirty parts of light liquid isoparaffin was added to 100 parts of the cosmetic base to give a mixture. The mixture was kneaded at normal temperature, was then packed in a resin plate container, and was dried to remove the light liquid isoparaffin to give an eyebrow (solid).

The eyebrow (solid) of Example 13 was evaluated with a brush according to the evaluation method of the above-described Examples and was rated. As a result, the eyebrow exhibited excellent ease of loosening of the cosmetic, smooth feeling in use, and adhesiveness to the skin and also exhibited no change in usability in continuous use and had excellent filling and molding properties and drop strength.

Example 14: Foundation (Component): (%)
1. Black iron oxide: 0.5
2. Red iron oxide: 0.5
3. Yellow iron oxide: 1.5
4. Amino-modified silicone-treated titanium oxide of Production Example 1: 15
5. Amino-modified silicone-treated mica [1] of Production Example 2: 25
6. Sericite: balance
7. Polyethylene terephthalate powder *14: 3
8. Dimethylpolysiloxane (3%)-treated plate-like titanium oxide: 7
9. Anhydrous silicic acid (spherical, average particle diameter: 3.5 µm): 5
10. Diisostearyl malate: 5
11. Squalane: 1
12. Tridecyl trimellitate: 1
13. Dimethylpolysiloxane (10 mm$^2$/s at 25° C.): 1
14. (Sodium acrylate/sodium acryloyldimethyl taurate) copolymer *7: 2
15. Magnesium aluminum silicate *9: 2
*14: Snowleaf P (manufactured by Ohken Co., Ltd.)
(Production Method)
A. Components (1) to (9) were uniformly mixed.
B. A uniform mixture of components (10) to (15) was added to the mixture prepared in the step A, followed by uniform dispersion and crushing to give a cosmetic base.
C. A hundred parts of purified water was added to 100 parts of the cosmetic base to give a mixture. The mixture was kneaded at normal temperature and was then packed in a metal plate. The volatile solvent was collected with an absorber, such as a porous press head, while compressing the mixture. The mixture was dried to remove the purified water to give a foundation.

The foundation of Example 14 was evaluated with a mat according to the evaluation method of the above-described Examples and was rated. As a result, the foundation exhibited excellent ease of loosening of the cosmetic, smooth feeling in use, and adhesiveness to the skin and also exhibited no change in usability in continuous use and had excellent filling and molding properties and drop strength.

Example 15: Blusher (Component): (%)
1. Perfluorooctyl triethoxysilane (3%)-treated yellow iron oxide: 0.5
2. Perfluorooctyl triethoxysilane (3%)-treated black iron oxide: 0.1
3. Perfluorooctyl triethoxysilane (3%)-treated red iron oxide: 3
4. Red 226: 2
5. Amino-modified silicone-treated mica *1: 20
6. Mica *2: balance
7. Red iron oxide-coated mica titanium *15: 15
8. Black iron oxide-coated mica titanium *13: 5
9. Polyethylene terephthalate powder *14: 5
10. Diglyceryl triisostearate: 1
11. 2-Ethylhexyl hydroxystearate: 1
12. Heavy liquid isoparaffin: 1
13. Squalane: 2
14. Perfluoropolymethyl isopropyl *16: 1
15. (Sodium acrylate/sodium acryloyldimethyl taurate) copolymer *7: 1
16. Magnesium aluminum silicate *9: 1
*15: CLOISONNE CERISE FLAMBE 550Z (manufactured by BASF SE, red iron oxide (48%)-containing mica)
*16: Fomblin HC/04 (manufactured by Ausimont)
(Production Method)
A. Components (1) to (9) were uniformly mixed.
B. A uniform mixture of components (10) to (16) was added to the mixture prepared in the step A, followed by uniform dispersion and crushing to give a cosmetic base.
C. Fifty parts of decamethyl cyclopentasiloxane was added to 100 parts of the cosmetic base to give a mixture. The mixture was kneaded at normal temperature, was then packed in a resin plate container, and was dried to remove the decamethyl cyclopentasiloxane to give a blusher.

The blusher of Example 15 was evaluated with a brush, and the results were evaluated according to the evaluation method of the above-described Examples and were rated. As a result, the blusher exhibited excellent ease of loosening of the cosmetic, smooth feeling in use, and adhesiveness to the skin and also exhibited no change in usability in continuous use and had excellent filling and molding properties and drop strength.

Example 16

Eyeliner (Component): (%)
1. Black iron oxide: 10
2. Red iron oxide: 3
3. Yellow iron oxide: 3
4. Amino-modified silicone-treated mica *1: 20
5. Amino-modified silicone-treated talc [2] of Production Example 6: 5
6. Sericite: balance
7. Black iron oxide-coated mica titanium *13: 20
8. Polyethylene terephthalate powder *14: 5
9. Diisostearyl malate: 4
10. Liquid paraffin: 1
11. Diglyceryl diisostearate: 4
12. (Sodium acrylate/sodium acryloyldimethyl taurate) copolymer *7: 1
13. Magnesium aluminum silicate *9: 2
(Production Method)
A. Components (1) to (8) were uniformly mixed.
B. A uniform mixture of components (9) to (13) was added to the mixture prepared in the step A, followed by uniform dispersion and crushing to give a cosmetic base.
C. One hundred and fifty parts of water containing 5% alcohol was added to 100 parts of the cosmetic base to give a mixture. The mixture was kneaded at normal temperature, was then packed in a resin plate container, and was dried to remove the water-alcohol solution to give an eyeliner.

The eyeliner of Example 16 was evaluated with a chip according to the evaluation method of the above-described Examples and was rated. As a result, the eyeliner exhibited excellent ease of loosening of the cosmetic, smooth feeling in use, and adhesiveness to the skin and also exhibited no change in usability in continuous use and had excellent filling and molding properties and drop strength.

The invention claimed is:

1. A solid powder cosmetic comprising components (A) to (C):
    (A) an amino-modified silicone-treated powder;
    (B) a (sodium acrylate/sodium acryloyldimethyl taurate) copolymer; and
    (C) a water-swelling clay mineral.

2. The solid powder cosmetic according to claim 1, wherein a content of component (B) is 0.1% to 2% by mass.

3. The solid powder cosmetic according to claim 2, wherein a content of component (C) is 0.1% to 2% by mass.

4. The solid powder cosmetic according to claim 3, wherein a content of component (A) is 80% to 99% by mass.

5. The solid powder cosmetic according to claim 2, wherein a content of component (A) is 80% to 99% by mass.

6. The solid powder cosmetic according to claim 2, further comprising an oily component at a content of 10% by mass or less.

7. The solid powder cosmetic according to claim 1, wherein a content of component (C) is 0.1% to 2% by mass.

8. The solid powder cosmetic according to claim 7, wherein a content of component (A) is 80% to 99% by mass.

9. The solid powder cosmetic according to claim 1, wherein a content of component (A) is 80% to 99% by mass.

10. The solid powder cosmetic according to claim 1, further comprising an oily component at a content of 10% by mass or less.

11. The solid powder cosmetic according to claim 1, wherein a content of component (B) is 0.1% to 2% by mass.

12. The solid powder cosmetic according to claim 11, wherein a content of component (C) is 0.1% to 2% by mass.

13. The solid powder cosmetic according to claim 12, wherein a content of component (A) is 80% to 99% by mass.

14. The solid powder cosmetic according to claim 11, wherein a content of component (A) is 80% to 99% by mass.

15. The solid powder cosmetic according to claim 1, wherein a content of component (C) is 0.1% to 2% by mass.

16. The solid powder cosmetic according to claim 15, wherein a content of component (A) is 80% to 99% by mass.

17. The solid powder cosmetic according to claim 1, wherein a content of component (A) is 80% to 99% by mass.

18. The solid powder cosmetic according to claim 1, further comprising an oily component at a content of 10% by mass or less.

19. A solid powder cosmetic comprising the following-components (A) to (C):
    (A) an amino-modified silicone-treated powder,
    (B) a (sodium acrylate/sodium acryloyldimethyl taurate) copolymer, and
    (C) a water-swelling clay mineral
    wherein the solid powder cosmetic is produced by mixing a cosmetic base containing the components (A) to (C) with a solvent to form a slurry, and filling a container with the slurry, and then removing the solvent.

* * * * *